United States Patent [19]
Huff et al.

[11] Patent Number: 5,686,312
[45] Date of Patent: Nov. 11, 1997

[54] METHOD OF DETERMINING EMISSIONS FROM POWDER COATINGS

[75] Inventors: Robert W. Huff; Susan M. Miller, both of North Royalton; Joanne M. Szydlowski, Chagrin Falls, all of Ohio

[73] Assignee: Ferro Corporation, Cleveland, Ohio

[21] Appl. No.: 593,208

[22] Filed: Jan. 29, 1996

[51] Int. Cl.$^6$ .................................................. G01N 30/12
[52] U.S. Cl. .......................... 436/161; 436/55; 427/384
[58] Field of Search ........................... 427/195, 372.2, 427/384, 385.5, 386, 379, 8; 436/85, 161, 167, 55

*Primary Examiner*—Lyle A. Alexander
*Attorney, Agent, or Firm*—Rankin, Hill, Lewis & Clark

[57] ABSTRACT

A method for reducing residue formation caused by volatile materials during the curing of powder coating compositions which includes the steps of applying different powder coating compositions to separate bases; placing each coated base in a separate extraction chamber; placing each separate extraction chamber in a curing oven; heating the coated base in its respective extraction chamber in the curing oven to curing temperature to cure the coating composition, and simultaneously flowing a stream of air through the respective extraction chamber to capture volatile emissions from the volatile materials in the air stream during the curing process; simultaneously flowing the respective stream of air out of the curing oven and chilling the stream to condense the volatile emissions from each of the compositions to a collectable form; determining the quantity of the emitted product from each of the compositions; and comparing the quantity of emitted product from each of the compositions to determine the composition that produced the least emissions.

9 Claims, 2 Drawing Sheets

5,686,312

METHOD OF DETERMINING EMISSIONS FROM POWDER COATINGS

FIELD OF DISCLOSURE

This invention relates to powder coatings and the like wherein a layer of coating particles is applied to the surface of a base such as a panel or partition formed of sheet metal, and then heated in an oven or similar device to cure the particles to form a durable surface coating. More particularly, the invention relates to a process for determining, in a specific application, a powder coating formulation that minimizes the formation of a residue on the walls of the heating device during the curing step.

BACKGROUND OF THE INVENTION

In the manufacture of many types of products such as, for example, laundry and kitchen appliances, automotive parts, and other fabricated parts, a durable protective coating is applied to certain metal surfaces. A coating of an acrylic resin is particularly suitable for example, in the case of automotive parts.

One process for applying such coating materials includes the application of a layer of powder coating particles to the surface of the base metal. The resulting product is then placed in a curing oven to cure the powder coating particles. This results in a tough, durable, protective coating.

The powder coating compositions used in these applications usually include a component that functions as a crosslinker which reacts with the base resin during the curing process. The amount of crosslinker to be included must be sufficient to achieve optimum curing of the coating material. Under cure conditions, volatile materials such as the crosslinker can sublime or volatilize from the coating material. More particularly, any excess crosslinker that does not chemically react during the curing process generally vaporizes and eventually condenses to leave an undesirable residue.

In the past, the amount of crosslinker to be used in the composition has been selected based on trial and error type experimentation. In this trial and error approach, some formulations produce excessive amounts of volatile materials which form residue on the surface of the heating device (cure oven) and related equipment employed in the curing process. Removal of this residue is burdensome and time consuming. Also, it has an undesirable effect on prospective purchasers of the coating system. While the reduction of, or elimination of this residue is extremely desirable, no means has been available to determine the precise amount of crosslinker or other volatile materials required for curing under a particular set of conditions.

Laboratory experimentation has determined that controlling the ratio of the surface area of the base to be coated to the amount by weight of the vapor producing crosslinker achieves results that can be consistently reproduced. However, no method has been available for determining a minimum quantity of vapor producing materials to be employed under particular circumstances.

The present invention provides a method to minimize the amount of volatile materials formed during curing so that the formation of the unwanted residue can be minimized or eliminated in a number of particular circumstances with variations in composition and curing conditions.

SUMMARY OF THE INVENTION

It is among the objects of the present invention to reduce the formation of a residue resulting from the vaporization of excess crosslinker or other volatile materials used in the formulation of powder coating compositions to be applied in the form of a layer of powder to the surface of a substrate or base and then heated in an oven to cure the resin particles.

Another object is to provide a procedure for determining the optimum resin/crosslinker balance in the powder coating composition so as to reduce vaporization of excess crosslinker and thus reduce the formation of residue during curing.

In accordance with the invention, an optimum quantity of vapor producing material used in the curable powder coating composition is determined by the steps of:

(a) preparing a plurality of experimental curable powder coating compositions with varying quantities of a vapor producing material and applying each of the compositions to a separate base or substrate at a specific predetermined film thickness;

(b) placing each coated base in a separate extraction chamber (c) placing each separate extraction chamber in a curing oven;

(d) heating the coated base in its respective extraction chamber in the curing oven to curing temperature to cure the coating composition, and simultaneously flowing a stream of atmosphere through the respective extraction chamber to capture volatile emissions from the volatile material in the flowing stream during the curing process, (e) simultaneously flowing the respective stream of atmosphere out of the curing oven and chilling the stream to condense the volatile emissions from each of the compositions to a collectable form;

(f) determining the quantity of the emitted product from each of the compositions; and (g) comparing the quantity of emitted product from each of the compositions that produce a satisfactorily cured coating, to determine the composition that produced the least emissions.

The invention has particular utility in connection with the use of acrylic resin based powder coating composition wherein the crosslinker used is dodecanedioic acid (DDA). During the curing step excess DDA is volatilized, and upon cooling, the volatilized DDA condenses to form a residue of particles on the surface of the heating device, such as a cure oven, and related heating equipment. By sampling a number of powder coating compositions containing various amounts of the crosslinker to determine in each case the amount of vapor that is formed, an optimum composition can be selected for the particular conditions involved.

DESCRIPTION OF THE PREFERRED EMBODIMENT

Figure 1:
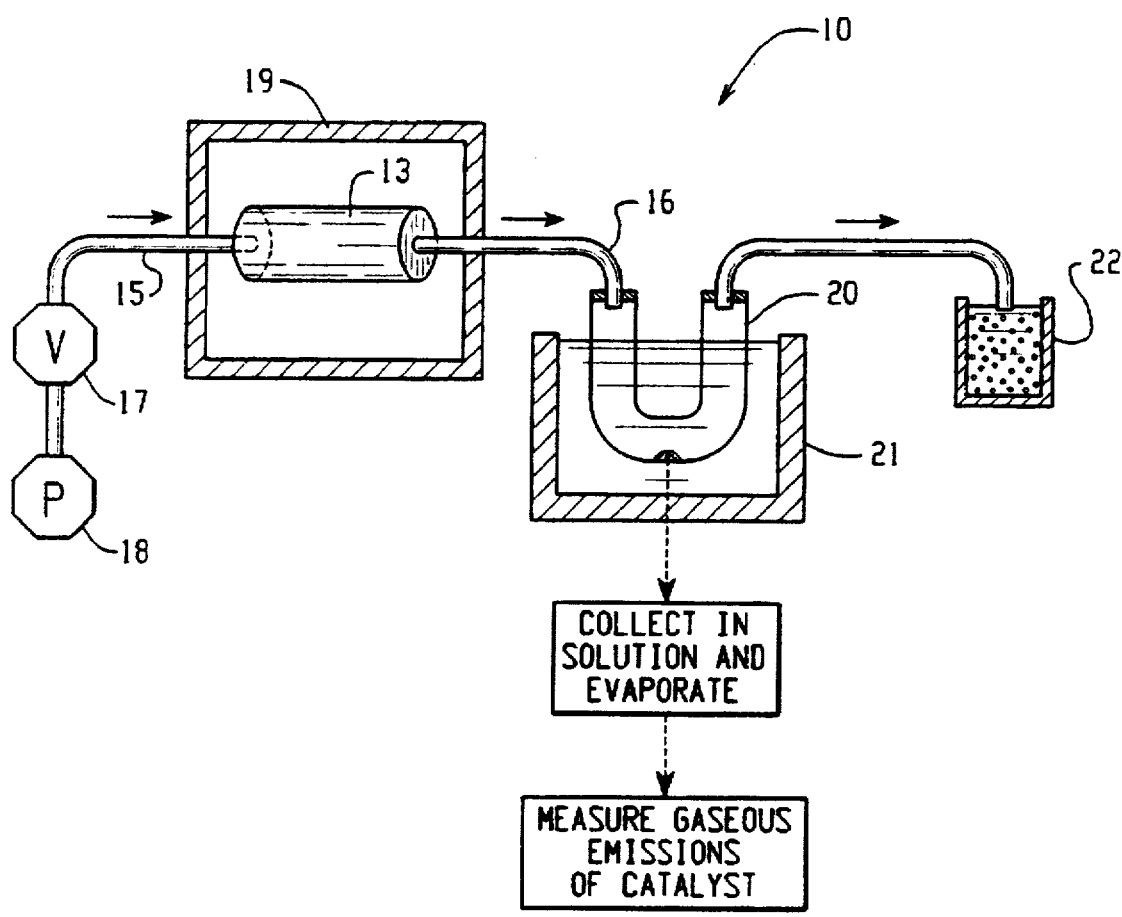
FIG. 1 is a schematic diagram illustrating the sampling procedure and apparatus used to determine the optimum quantity of volatile material in a powder coating composition used in practicing the method of the invention.

Referring more particularly to FIG. 1, there is shown a typical apparatus 10 for analyzing a particular powder coating composition under actual conditions used in the manufacture of a product having a protective coating layer formed on certain surfaces. The sampling procedure includes the preparation of a number of sample plates (not shown) such as aluminum strips to provide a base for the powder coating composition. The plates are coated to a particular film thickness and slightly heated (to facilitate cutting of the coated aluminum to the desired size), for example, with an acrylic resin based powder coating composition, each particular plate having a different quantity of a vapor-producing material such as DDA in the composition.

The coated plates are placed in an extraction chamber 13 which may be formed, for example, of stainless steel and which is provided with fittings on each end for flowing air through the chamber (only one chamber is illustrated in FIG. 1).

For example, the extraction chamber may be formed of a cylindrical length of tubing with endcaps screwed in place over each end and being drilled and tapped for standard threaded fittings. The fittings must be free of leaks and are preferably tested prior to use. One end fitting is connected to an inlet line 15 and the other to an outlet line 16. The outside end of the inlet line 15 is connected to a flow control valve 17 which controls the flow from a compressor 18.

The plates with a powder coating composition sprayed thereon, are inserted in respective extraction chambers and the chambers are then placed in a curing oven 19, preferably the type of oven in which the product being manufactured is to be placed for curing of the powder coating composition.

The oven temperature is then raised to the predetermined curing temperature and a carefully controlled airflow is transmitted through each of the extraction chambers being utilized. The airflow exits the extraction chamber and flows out of the oven 19 to a U-tube 20.

The U-tube is located in a liquid nitrogen dewar 21 to chill the flowing stream. The air flow is monitored using, for example, a bubble flow meter 22 connected to the end of the glass U-tube 20. This procedure is continued during the time period required for the curing of the powder coating composition. For example, a period of one hour would be typical.

During the curing period, any excess volatile material is vaporized and picked up in the flowing air stream. Thus, the vaporized (excess) component is extracted from the chamber and carried in the flowing air stream to the U-tube 20. Chilling of the flowing stream in the U-tube results in condensation (and in some cases crystallization) of the extracted excess volatile material, primarily in the bottom loop of the U-tube.

Once the curing time period expires, the oven 19 is permitted to cool to ambient temperature and the airflow is cut off. It should be appreciated that cooling to ambient temperature is not required.

Then the U-tube 20 is disconnected and flushed with a suitable rinse such as pyridine. The resulting wash may be collected in a vial and then evaporated to dryness.

After suitable handling, the resulting composition may be analyzed, for example, by gas chromatography to measure the quantity of the volatile material that was vaporized and collected. The results are then compared and the quantity of volatile material that resulted in a minimum production of vapor emission is determined. With this data, a powder coating composition may be selected for the particular circumstances involved and assuming that the curing conditions are repeated uniformly for the particular product, the process can be performed with significant reduction in the accumulation of residue on the walls of the heating device and related equipment used to cure the coating composition.

Figure 2:
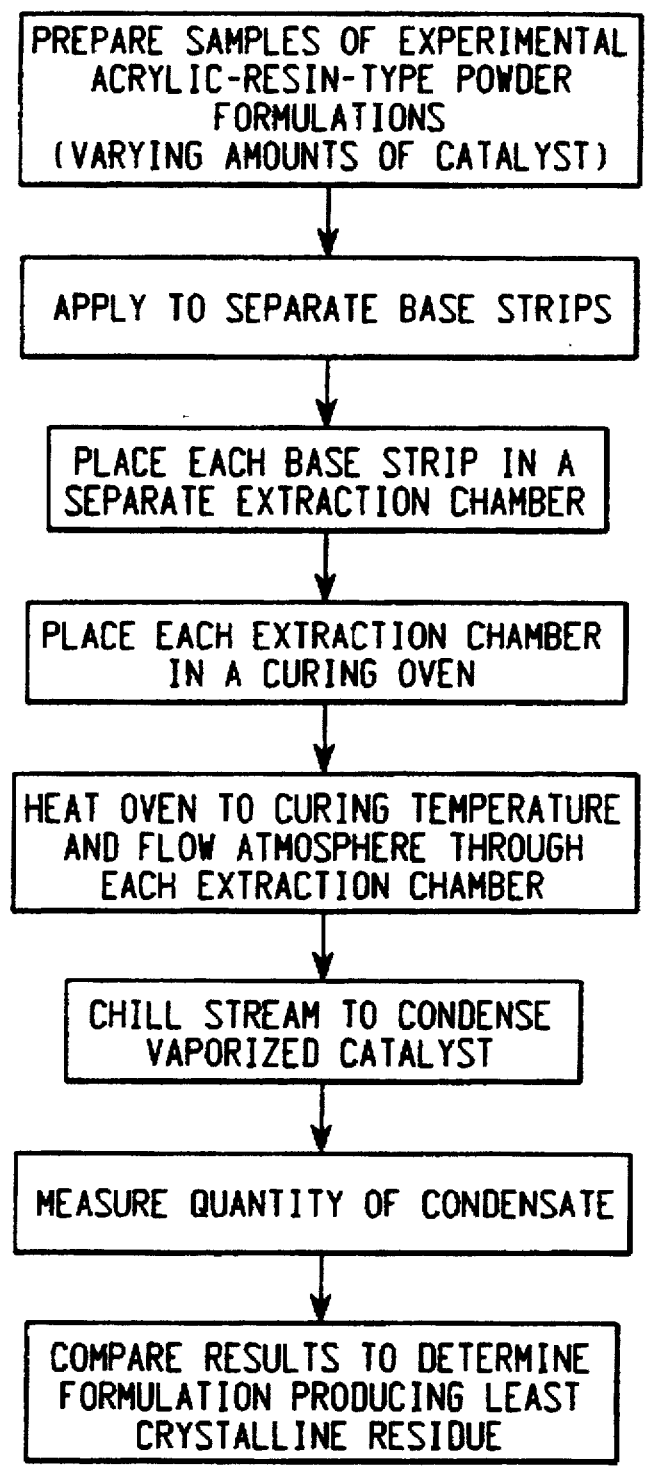
FIG. 2 is a block diagram illustrating the various sequential steps for practicing the broad method of the invention.

FIG. 2 illustrates the various steps that one can employ when practicing the method of the present invention.

The following example will serve to illustrate the novel features and advantages of the present invention. While this example will show one skilled in the art how to operate within the scope of this invention, it is not to serve as a limitation on the scope of the invention for such scope is only defined in the claims below.

EXAMPLE

Two aluminum strips were sprayed to a depth of 2.8 mil with an acrylic resin based powder coating composition including a standard formulation identified as A and an experimental formulation identified as B. The strips were then slightly heated to facilitate cutting of the strips to a size of about 3.3 cm×22 cm. Both formulations included a quantity of a crosslinker in the form of a dodecanedioic acid (DDA), a portion of which reacts during the curing process. (Any excess or unreacted DDA vaporizes during curing of the coating composition and subsequent cooling of the vapor causes condensation thereof to produce a residue).

The coated strips were each placed in a separate extraction chamber comprising a stainless steel tube about 8 inches long and 1¾ inches in diameter. Each chamber had drilled and tapped end plugs for receiving line connectors.

The two stainless steel extraction chambers were placed in a curing oven, each having an inlet line for atmosphere connected to one end plug and an exhaust line for atmosphere connected to the other end plug. All of the respective flow lines extended through the furnace wall to the outside of the furnace.

Provision was made to pass atmosphere at a controlled pressure through each inlet line to the respective extraction chamber, the atmosphere being preheated by passing it through a four foot length of ¹/₁₆ inch diameter coiled stainless steel tubing positioned within the curing oven.

The flow of atmosphere passed through the respective extraction chambers and was exhausted through the respective outlet lines. The opposite end of each outlet line was connected to a ³/₁₆ inch diameter glass U-tube. The U-tube was placed in a liquid nitrogen dewar. The flow rate was monitored at the downstream end of the U-tube by a bubble-type flow meter.

The curing oven was heated to a temperature of about 163° C. and the flow rate for the atmosphere was adjusted to about 120–170 ml/minute. This temperature and flow rate were maintained for about one hour. During this time, any vapor produced in the two extraction chambers was extracted therefrom with the flow of atmosphere and then condensed in the respective U-tube to form a crystalline residue.

When the extraction was completed, both the U-tubes and the outlet tubes were flushed with pyridine. The washes were collected in a vial and evaporated to dryness under a nitrogen stream with very gentle warming.

One ml of a 1000 ug/ml internal standard solution of erucis acid was added to the vial and evaporated to dryness. The contents of a 1 ml ampule of BSTFA+1% TMCS was added and the vial was capped and heated at 80° C. for 15 minutes.

The resulting solution was then injected into a gas chromatography unit under the following condition:

Columns: 30m×0.25 mm ID J&W DB-5, 0.25 um
Carrier: He at 38.5 cm/min (measured at 50° C.)
Oven: 50° C. for 1 min 50°–270° C. at 10°/min 270° hold for 7 min Injection: Split 2 ul 30:1, 300° C.
Detector: FID, 300° C.
Table I below shows the results of the analysis:

TABLE I

| Sample | DDA Evolution | Standard Deviation |
|---|---|---|
| A (2.8 mil) | 477 | 66 |
| B (2.8 mil) | 125 | 26 |

These results show the sample formulation identified as B yielding a statistically significant reduction in DDA evolution and thus in residue formation.

It will be appreciated that the present invention is capable of being used to measure a variety of volatile materials other than DDA. Specifically, for example, the invention may be employed to measure/detect volatile materials in the powder coating composition such as deblocking agents like caprolactam, degassing agents such as benzoin and unwanted impurities such as volatile residual solvents. Further, it will be appreciated that the teachings of the present invention are applicable to a variety of powder coating compositions and thus the invention is not limited to acrylic resin based systems.

While the invention has been shown and described with respect to specific embodiments of the method and apparatus thereof, this is intended for the purpose of illustration rather than limitation and other variations and modifications of the specific method and apparatus herein shown and described will be apparent to those skilled in the art all within the intended spirit and scope of the invention. Accordingly, the patent is not to be limited in scope and effect to the specific method and apparatus herein shown and described nor in any other way that is inconsistent with the extent to which the progress in the art has been advanced by the invention.

We claim:

1. A method for reducing residue formation caused by vapor-producing materials during curing of powder coating compositions by minimizing the quantity of a vapor-producing materials that is required in the initial curable powder coating composition, comprising the steps of:

a. preparing a plurality of curable powder coating compositions with varying quantities of a vapor-producing materials and applying each of said compositions to a separate base;

b. placing each coated base in a separate extraction chamber;

c. placing each separate extraction chamber in a curing oven;

d. heating said coated base in its respective extraction chamber, in said curing oven to curing temperature to cure said coating, and simultaneously flowing a stream of air through said respective extraction chamber to capture volatile emissions from said vapor-producing materials in said air stream during said curing process;

e. simultaneously flowing said respective stream of air out of said curing oven and chilling said stream to condense said volatile emissions from each of said compositions to a collectable form;

f. determining the quantity of said emitted product from each of said compositions; and g. comparing the quantity of emitted product from each of said compositions that produce a satisfactorily cured coating, to determine the composition that produced the least emissions.

2. A method as defined in claim 1 wherein said vapor-producing material is dodecanedioic acid.

3. A method as defined in claim 1 wherein said powder coating composition includes an acrylic resin.

4. A method as defined in claim 1 wherein the quantity of said collected condensate is determined by gas chromatography.

5. A method for analyzing powder coating compositions to determine the quantity of excess volatile material that is vaporized during curing comprising the steps of:

a. preparing a plurality of curable powder coating compositions with varying quantities of a volatile material and applying each of said compositions to a separate substrate;

b. placing each coated substrate in a separate extraction chamber;

c. placing each separate extraction chamber in a curing oven;

d. heating said coated substrate in its respective extraction chamber, in said curing oven to curing temperature to cure said coating, and simultaneously flowing a stream of atmosphere through said respective extraction chamber to capture volatilized emissions in said stream during said curing process;

e. simultaneously flowing said respective stream out of said curing oven and chilling said stream to condense said volatile emissions from each of said compositions to a collectable form; and f. determining the quantity of said collected condensate from each of said compositions.

6. A method as defined in claim 5 wherein said volatile material is a material selected from the group consisting of a crosslinker, a degassing agent, a deblocking agent and mixtures of two or more thereof.

7. A method as defined in claim 5 wherein said powder coating composition includes an acrylic resin.

8. A method as defined in claim 5 wherein the quantity of said collected condensate is determined by gas chromatography.

9. A method as set forth in claim 6 wherein said crosslinker comprises dodecandedioic acid.

* * * * *